United States Patent
Ternes et al.

(10) Patent No.: US 9,586,048 B2
(45) Date of Patent: Mar. 7, 2017

(54) METHODS AND APPARATUS FOR APNEA THERAPY STIMULATION

(71) Applicant: Cardiac Pacemakers, Inc., St. Paul, MN (US)

(72) Inventors: David J. Ternes, Roseville, MN (US); Pramodsingh Hirasingh Thakur, Woodbury, MN (US); Stephen B. Ruble, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/638,221

(22) Filed: Mar. 4, 2015

(65) Prior Publication Data

US 2015/0283383 A1 Oct. 8, 2015

Related U.S. Application Data

(60) Provisional application No. 61/975,090, filed on Apr. 4, 2014.

(51) Int. Cl.
*A61N 1/00* (2006.01)
*A61N 1/36* (2006.01)
(Continued)

(52) U.S. Cl.
CPC ........ *A61N 1/36139* (2013.01); *A61B 5/0205* (2013.01); *A61B 5/4818* (2013.01);
(Continued)

(58) Field of Classification Search
USPC ..................................... 607/18, 20
See application file for complete search history.

(56) References Cited

U.S. PATENT DOCUMENTS 7,225,021 B1 * 5/2007 Park ................... A61N 1/3601
600/301
7,787,946 B2 * 8/2010 Stahmann ............ A61B 5/0031
607/3

(Continued)

FOREIGN PATENT DOCUMENTS

| CN | 202505987 U | 10/2012 |
|---|---|---|
| WO | WO-2010057286 A1 | 5/2010 |
| WO | WO-2015153046 A1 | 10/2015 |

OTHER PUBLICATIONS

"International Application Serial No. PCT/US2015/018700, International Search Report mailed Jun. 3, 2015", 4 pgs.

(Continued)

*Primary Examiner* — Nicole F Johnson
(74) *Attorney, Agent, or Firm* — Schwegman Lundberg & Woessner, P.A.

(57) ABSTRACT

Disclosed herein, among other things, are methods and apparatus related to apnea therapy. One aspect of the present subject matter provides a method for apnea directed therapy. The method includes receiving a signal indicative of a real-time determination of type of an apnea event for a patient during the apnea event, and using the signal to select appropriate therapy to be applied to the patient during the apnea event to treat the apnea event, and to withhold inappropriate therapy. The therapy is applied in a closed loop system, in various embodiments. In various embodiments, the signal includes a determination of whether the apnea event is primarily an obstructive sleep apnea (OSA) event or primarily a central sleep apnea (CSA) event.

14 Claims, 12 Drawing Sheets

(51) Int. Cl.
  *A61N 1/365* (2006.01)
  *A61B 5/00* (2006.01)
  *A61B 5/0205* (2006.01)
  *A61N 1/39* (2006.01)
  *A61N 1/05* (2006.01)

(52) U.S. Cl.
  CPC ............ *A61B 5/4836* (2013.01); *A61B 5/686* (2013.01); *A61N 1/3611* (2013.01); *A61N 1/36053* (2013.01); *A61N 1/36542* (2013.01); *A61N 1/0551* (2013.01); *A61N 1/3601* (2013.01); *A61N 1/36078* (2013.01); *A61N 1/3956* (2013.01)

(56) References Cited

U.S. PATENT DOCUMENTS

| | | | |
|---|---|---|---|
| 8,551,010 | B2 | 10/2013 | Pu et al. |
| 8,560,072 | B2 | 10/2013 | Caparso et al. |
| 2005/0074741 | A1 | 4/2005 | Lee et al. |
| 2006/0142815 | A1 | 6/2006 | Tehrani et al. |
| 2010/0286553 | A1* | 11/2010 | Feler ........................ A61B 5/05 600/554 |
| 2012/0029362 | A1 | 2/2012 | Patangay et al. |
| 2013/0041269 | A1 | 2/2013 | Stahmann et al. |

OTHER PUBLICATIONS

"International Application Serial No. PCT/US2015/018700, Written Opinion mailed Jun. 3, 2015", 5 pgs.

Argod, Jerome, et al., "Differentiating Obstructive and Central Sleep Respiratory Events through Pulse Transit Time", AM J RESPIR CRIT CARE MED; 158, (1998), 1778-1783.

"Remede implantable device system shows "promising" results in the treatment of central sleep apnoea, pilot study shows", Cardiac Rhythm News, http://www.cxvascular.com/crn-latest-news/cardiac-rhythm-news—latest-news/remede-imp . . . 2 pages, latest print date Mar. 3, 2015.

Abraham, W.T., et al., "The Effects of Chronic Implanted Transvenous Phrenic Nerve Stimulation in Central Sleep Apnea: The Remede System Pilot Study", Lipids and Inflammation / Heart Failure: Basic Mechanisms; European Heart Journal, (Aug. 1, 2013), 769.

DiMarco, Anthony F., et al., "Phrenic Nerve Pacing Via Intramuscular Diaphragm Electrodes in Tetraplegic Subjects", Chest. 2005;12(2):671-678, Feb. 2005.

Franke, Manfred, et al., "Selective Nerve Stimulation Using Presynaptic Terminal Depletion Block", U.S. Appl. No. 61/928,732, filed Jan. 17, 2014.

Kaiser, Chris, "Device Cuts Central Sleep Apnea Events", MedPage Today; http://www.medpagetoday.com/MeetingCoverage/HFSA/41796?xid=nl_mpt_DHE_2013-09-24, (Sep. 23, 2013), 3.

Mietus, JE, et al., "Detection of Obstructive Sleep Apnea from Cardiac Interbeat Interval Time Series", Physionet, http://www.physionet.org/physiotools/apdet/apdet.shtml, 5 pages, latest print date Mar. 2, 2015.

Teerlink, John, et al., "ATOMIC-AHF: Acute Treatment with Omecamtiv Mecarbil to Increase Contractility in Acute Heart Failure: Results from ATOMIC-AHF", European Society of Cardiology; Session No. 709, (2013), 1-3.

Thakur, Pramodsingh Hirasingh, et al., "Discrimination of Apnea Type by Medical Device", U.S. Appl. No. 61/975,084, filed Apr. 4, 2014.

Thomas, RJ, et al., "Differentiating obstructive from central and complex sleep apnea using an automated electrocardiogram-based method", SLEEP, vol. 30, No. 12, 2007, (Jul. 2007), 1756-1769.

University Hospitals, Case Medical Center, "Electronic stimulation therapy for obstructive sleep apnea is safe, effective, new study suggests", Science Daily; www.sciencedaily.com/releases/2013/06/130605144316.htm, (Jun. 5, 2013), 1.

* cited by examiner

METHODS AND APPARATUS FOR APNEA THERAPY STIMULATION

CLAIM OF PRIORITY

This application claims the benefit of priority under 35 U.S.C. §119(e) of U.S. Provisional Patent Application Ser. No. 61/975,090, filed on Apr. 4, 2014, which is herein incorporated by reference in its entirety.

CROSS REFERENCE TO RELATED APPLICATION

This application is related to commonly assigned. U.S. Patent Application Ser. No. 61/975,084, entitled "DISCRIMINATION OF APNEA TYPE BY MEDICAL DEVICE", filed on Apr. 4, 2014, which is hereby incorporated by reference in its entirety.

TECHNICAL FIELD

This application relates generally to medical devices and, more particularly, to systems, devices, methods and apparatus for apnea therapy stimulation.

BACKGROUND

Respiratory diseases include disorders that affect breathing during sleep. Examples of respiratory disorders include central sleep apnea (CSA) and obstructive sleep apnea (OSA). Sleep apnea refers to the cessation of breathing during sleep. CSA is associated with incorrect sensing of carbon dioxide or oxygen levels in the blood. If nerve receptors do not send the correct neural signals, in essence deceiving the brain by reporting incorrect levels of carbon dioxide or oxygen, an incidence of CSA can occur. OSA is associated with an obstruction of the upper airway. Both CSA and OSA have serious health consequences, including association with cardiac arrhythmias and worsening heart failure. Stimulation therapy for apnea differs depending upon whether the patient is deemed a CSA or OSA patient. However, a patient rarely has exclusively a single type of apnea. Both CSA and OSA episodes can occur in one patient over the course of a night in different degrees.

Therefore, there is a need in the art for improved apnea therapy stimulation by tailoring therapy to the specific type of apnea in progress.

SUMMARY

Disclosed herein, among other things, are methods and apparatus related to apnea therapy. One aspect of the present subject matter provides a method for apnea directed therapy. The method may include receiving a signal indicative of a real-time or near real-time determination of type of an apnea event for a patient during the apnea event, and using the signal to select appropriate electrical stimulation therapy to be applied to the patient during the apnea event to treat the apnea event. The electrical stimulation therapy may be applied in a closed loop system, in various embodiments. In various embodiments, the signal may include a determination of whether the apnea event is primarily an obstructive sleep apnea (OSA) event or primarily a central sleep apnea (CSA) event.

One aspect of the present subject matter provides an implantable medical device for apnea directed therapy. The device may include an input configured to receive a signal indicative of a real-time or near real-time determination of type of an apnea event for a patient during the apnea event. In various embodiments, the device may include a processor adapted to be connected to the input, the processor configured to use the signal to select, withhold, or both select and withhold, therapy to be applied to the patient during the apnea event to treat the apnea event, and configured to control a stimulator to apply the therapy in a closed loop system. In various embodiments, OSA therapy is delivered and CSA therapy is withheld if the apnea event is determined to be primarily an OSA event, and CSA therapy is delivered and OSA therapy is withheld if the apnea event is determined to be primarily a CSA event.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
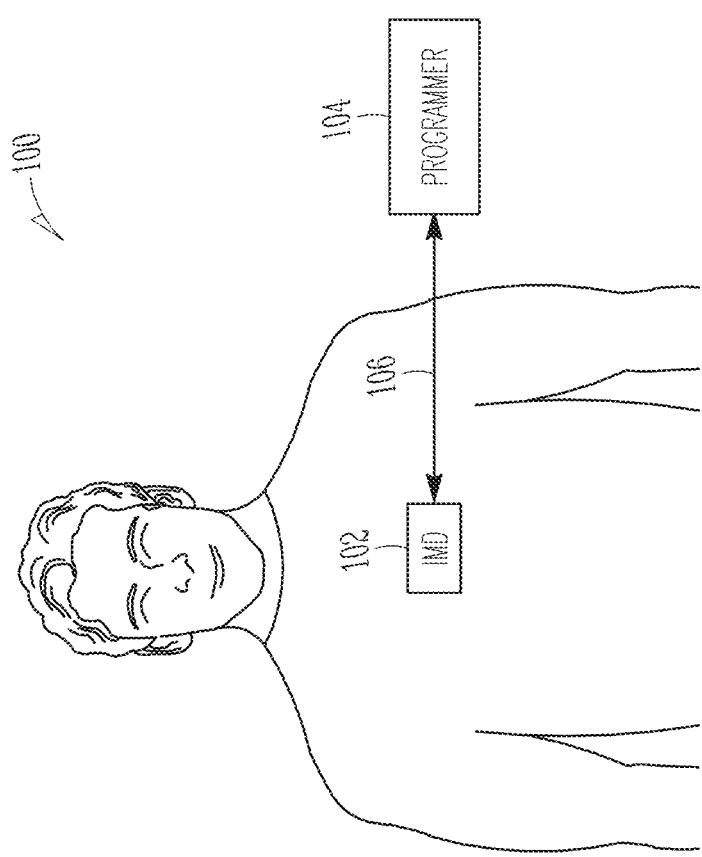
FIG. 1 illustrates an example of a therapy system with a programmer.

The following detailed description of the present invention refers to subject matter in the accompanying drawings which show, by way of illustration, specific aspects and embodiments in which the present subject matter may be practiced. These embodiments are described in sufficient detail to enable those skilled in the art to practice the present subject matter. References to "an," "one," or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Respiratory diseases include disorders that affect breathing during sleep. Examples of respiratory disorders include central sleep apnea (CSA) and obstructive sleep apnea (OSA). Sleep apnea refers to the cessation of breathing during sleep. CSA is associated with incorrect sensing of carbon dioxide or oxygen levels in the blood. If nerve receptors do not send the correct neural signals, in essence deceiving the brain by reporting incorrect levels of carbon dioxide or oxygen, an incidence of CSA can occur. OSA is associated with an obstruction of the upper airway. Both CSA and OSA have serious health consequences, including association with cardiac arrhythmias and worsening heart failure. CSA and OSA episodes can occur in a given patient over the course of a night albeit to different degrees. Typically, therapy for CSA is not effective for OSA, and therapy for OSA is not effective for CSA.

Disclosed herein, among other things, are methods and apparatus related to apnea therapy. One aspect of the present subject matter provides a method for apnea directed therapy. The method may include receiving a signal indicative of a real-time or near real-time determination of type of an apnea event for a patient during the apnea event, and using the signal to select appropriate electrical stimulation therapy to be applied to the patient during the apnea event to treat the apnea event. The electrical stimulation therapy may be applied in a closed loop system, in various embodiments. In various embodiments, the signal may include a determination of whether the apnea event is primarily an obstructive sleep apnea (OSA) event or primarily a central sleep apnea (CSA) event.

According to various embodiments, the signal may include a determination of whether the apnea event is primarily an obstructive sleep apnea (OSA) event or primarily a central sleep apnea (CSA) event. In various embodiments, determination may be actual classification based on real-time or near real-time sensors, or determination may be a likelihood (probabilistic) determination based on sensors and prior knowledge of patient condition. If the apnea event is determined to be primarily an OSA event, applying electrical stimulation therapy may include applying hypoglossal nerve stimulation, in an embodiment. In one embodiment, if the apnea event is determined to be primarily an OSA event, applying electrical stimulation therapy may include applying vagal nerve stimulation (VNS), such as laryngeal stimulation using selective fiber stimulation. If the apnea event is determined to be primarily an OSA event, applying electrical stimulation therapy may include applying hypoglossal nerve stimulation alone or in combination with applying VNS, in an embodiment. Other targets for OSA therapy include but are not limited to: glossopharyngeal, ans cervicalis, other nerves, and direct muscle stimulation. In various embodiments, a user input as to whether the patient is OSA or CSA dominant may be used to help weight the discrimination algorithm. Various users may provide input, including but not limited to a clinician or a patient.

If the apnea event is determined to be primarily a CSA event, applying electrical stimulation therapy may include applying phrenic nerve stimulation, applying stimulation using a cardiac rhythm management (CRM) device, or applying phrenic nerve stimulation in combination with using a CRM device in various embodiments. Other targets for CSA therapy include but are not limited to: direct diaphragmatic stimulation and transvascular stimulation of the diaphragm from inside the IVC (inferior vena cava). In one embodiment, if the apnea event is determined to be primarily a CSA event, applying electrical stimulation therapy may include applying VNS reflex cough stimulation. According to various embodiments, the method further includes selecting a stimulation site based on the received signal. Applying electrical stimulation may include using an implantable medical device (IMD) or using a remote stimulator controlled by the IMD, in various embodiments. Remote stimulators may include implantable and/or wireless remote stimulators, such as pacing seeds in various embodiments.

One aspect of the present subject matter provides an implantable medical device or devices for apnea directed therapy. The device may include an input configured to receive a signal indicative of a real-time or near real-time determination of type of an apnea event for a patient during the apnea event. These terms indicate that, although there may be some processing delays, the apnea discrimination is able to process the apneic events as they occur without an observable delay (e.g. real time) or with observable delays that are insignificant for processing the apneic events as they occur (near real time). In various embodiments, the device may include a processor adapted to be connected to the input, the processor configured to use the signal to select appropriate electrical stimulation therapy to be applied to the patient during the apnea event to treat the apnea event, and configured to control a stimulator to apply the electrical stimulation therapy in a closed loop system. According to various embodiments, the implantable medical device may include a neural stimulator, a CRM device, a subcutaneous implantable cardiac defibrillator (S-ICD), and/or a remote stimulator (such as a pacing seed) controlled by the implantable medical device. In various embodiments, the signal includes a determination (or likelihood) of whether the apnea event is primarily an obstructive sleep apnea (OSA) event or primarily a central sleep apnea (CSA) event. In various embodiments, OSA therapy is delivered and CSA therapy is withheld if the apnea event is determined to be primarily an OSA event, and CSA therapy is delivered and OSA therapy is withheld if the apnea event is determined to be primarily a CSA event. According to various embodiments, if the determination is ambiguous or of a mixed CSA/OSA, then if the device is configured for only CSA therapy or only OSA therapy, therapy is withheld. If the determination is ambiguous or of a mixed CSA/OSA, then if the device is configured to provide both CSA and OSA therapy, then both therapies will be selected and applied, in various embodiments. In one embodiment, a tiered approach is used for mixed CSA/OSA, by selecting and applying CSA therapy first to stimulate the diaphragm, which may be followed by OSA therapy to correct mechanical timing between the diaphragm and throat.

Some embodiments provide a system with a single implantable device configured to deliver both an obstructive apnea therapy and a central apnea therapy. By way of example and not limitation, a lead may be implanted from an implantable housing that contains one or more pulse generators to the hypoglossal nerve to provide the obstructive apnea therapy, and a lead may be implanted from the implantable housing that contains the one or more pulse generators to the phrenic nerve to provide the central apnea therapy. Some embodiments provide a first implantable device with its own hermetically sealed housing to provide the obstructive apnea therapy, and a second implantable device with its own hermetically sealed housing to provide the central apnea therapy. The control may be implemented in one or more of the first or second implantable devices, or another implantable device. Wired or wireless communication may be implemented between the devices.

In various embodiments, the present subject matter may provide closed loop central sleep apnea therapy, closed loop obstructive sleep apnea therapy, and/or both closed loop central and obstructive apnea therapy. Closed loop central sleep apnea therapy may include stimulation only on central sleep apnea events, stand-alone phrenic nerve stimulation or combined with CRM stimulation, and/or phrenic nerve stimulation direct on the nerve or using a nearby electrode such as using electrode(s) on an S-ICD lead or a lead similar to an S-ICD lead that passes near the phrenic nerve, in various embodiments. Closed loop obstructive sleep apnea therapy may include stimulation only on obstructive sleep apnea events, stand-alone hypoglossal nerve stimulator or combined with vagal nerve stimulation (VNS), and/or VNS laryngeal stimulation using selective fiber stimulation, in various embodiments. Combined closed loop central and obstructive apnea therapy may include using a stimulation site based on type of apnea event, such as using VNS laryngeal stimulation for obstructive events and VNS reflex cough stimulation for central events, using selective fiber stimulation in various embodiments. Other targets for OSA therapy include but are not limited to: hypoglossal nerve stimulation, glossopharyngeal, ans cervicalis, other nerves, and direct muscle stimulation. Other targets for CSA therapy include but are not limited to: phrenic nerve stimulation, stimulation using a cardiac rhythm management (CRM) device, or phrenic nerve stimulation in combination with using a CRM device, direct diaphragmatic stimulation and transvascular stimulation of the diaphragm from inside the IVC. Any of these may be combined for a given patient for a given apnea episode, in various embodiments. Various embodiments use remote stimulators, such as pacing seeds, controlled by the main IMD processor.

FIG. 1 illustrates an example of stimulation system 100. The system may include an external medical device, in various embodiments. Various types of external medical devices may be used without departing from the scope of the present subject matter. Various embodiments of the system may include an implantable medical device (IMD) 102 implanted into a patient's tissue and an external device such as a programmer 104 external to the patient's body. The programmer 104 and the IMD 102 may communicate via a telemetry link 106. Embodiments of the system without sensing are included within the scope of the present subject matter. The IMD 102 may be configured to deliver at least one apnea therapy. For example, the IMD may be configured to deliver at least one type of obstructive apnea therapy and/or maybe configured to deliver at least one type of central apnea therapy. Some embodiments may use more than one IMD to deliver the therapies. For example, one IMD may be used to deliver an obstructive apnea therapy and another IMD may be used to deliver a central apnea therapy. These IMDS may be configured to communicate over wired or over wireless (e.g. ultrasound, RF, inductive, conductive) channels. The system may be configured to provide a real-time or near real-time determination of type of an apnea event for a patient during the apnea event, and using the signal to select appropriate electrical stimulation therapy to be applied to the patient during the apnea event to treat the apnea event. This real-time or near real-time determination of type of an apnea event for a patient may be in one or more of the IMDS in system embodiments that have more than one IMD. Some embodiments may use external devices to monitor respiration and determine the apnea therapy type, and send the signals to the IMD(s) to provide the appropriate therapy.

Figure 2:
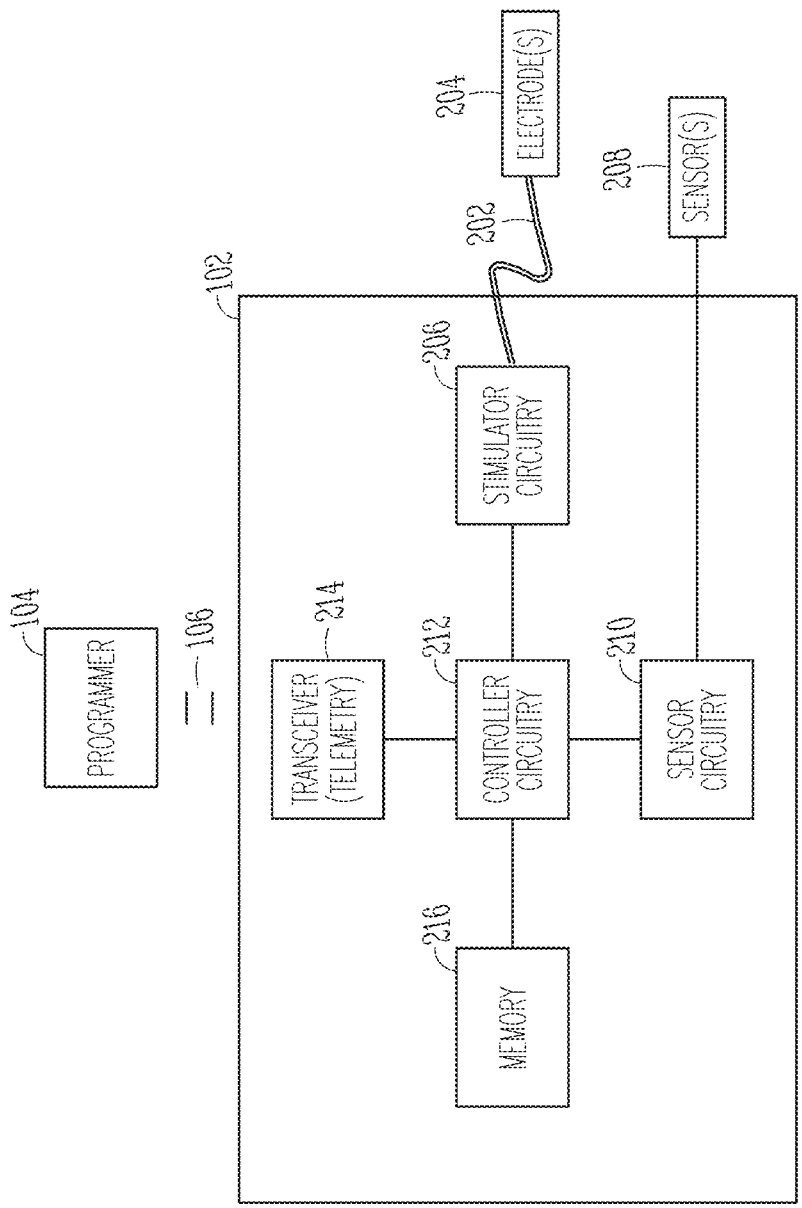
FIG. 2 illustrates an example of a system that includes an implantable medical device (IMD), such as the system of FIG. 1.

FIG. 2 illustrates an example of a system that includes an implantable medical device (IMD) and an external device such as the programmer 104 of FIG. 1. The IMD 102 may be coupled to at least a portion of a stimulation lead 202 having one or more electrodes 204 disposed on the lead 202. In various embodiments, the lead 202 may include cuff electrode(s), helical electrode(s), or other electrode configuration configured to deliver monopolar, bipolar or multipolar stimulation. The lead 202 may have dimensions suitable to place the one or more electrodes 204 proximate to a site of a neural pathway. For example, the electrode(s) may be intravascular electrodes or may be configured to otherwise be placed proximate to the nerve. For example, electrode(s) may be placed in the internal jugular vein (IJV) to stimulate a cervical vagus nerve, or may be placed in the carotid sheath at a site proximate the vagus nerve of a patient. Monopolar delivery occurs when a selected electrode is activated along with a reference electrode amongst the electrodes 204, so that electrical energy is transmitted between the selected electrode and the reference electrode. Monopolar delivery may also occur when one or more of the selected electrodes are activated along with a large group of electrodes located from the electrode(s) 204 so as to create a monopolar effect; that is, electrical energy is conveyed from the selected electrode(s) 204 in a relatively isotropic manner. Bipolar delivery occurs when two of the electrodes 204 are activated as anode and cathode, so that electrical energy is transmitted between the activated electrodes. Multipolar delivery occurs when multiple electrodes 204 are activated.

The IMD 102 may include a stimulation circuitry 206, sensor circuitry 210, a controller circuitry 212, a transceiver/telemetry circuitry 214, and a memory 216. The stimulation circuitry 206 is electrically coupled to the electrodes 204 using conductors of the stimulation lead 202. The stimulation circuitry 206 delivers electrical signals to the electrodes 204 to stimulate the desired target to provide stimulation. For example, the stimulation circuitry may be configured to deliver one or more obstructive apnea therapies. The stimulation circuitry may be configured to deliver one or more central apnea therapies. The stimulation circuitry maybe configured to deliver both obstructive and central apnea therapies. The programmer 104 may be used to program stimulation parameters into the memory 216. The controller circuitry 212 may use the programmed stimulation parameter to control the stimulator circuitry 206 to generate the stimulation that corresponds to the programmed stimulation parameters.

The IMD 102 may include one or more sensor(s) 208 for sensing physiological parameters such as cardiac contractions which may be used to determine heart rate (beats per minute or bpm) or rhythm information, tissue impedance (ohms), intrinsic atrial-ventricular (AV) delay (seconds), heart sounds, respiratory sounds, pressure, respiration, acceleration (activity and posture), nerve traffic, chemical parameters, or the like. The sensor(s) 208 can be located external to the IMD 102 housing, or encapsulated within the IMD 102 housing. The sensor(s) 208 can be attached to the sensor circuitry 210. The sensor circuitry 210 can include various components, such as instrumentation amplifiers, signal filters, etc., that process the electrical signals for determining the physiological parameters.

The sensor circuitry 210 feeds the physiological parameters to the controller circuitry 212. For example the sensory circuitry may be used to sense the parameters used to determine the type of apnea event. The controller circuitry 212 controls various operations of the IMD 102 and can include programmable microprocessors, microcontrollers, or the like. For example, the controller circuitry 212 may be programmed to perform therapy and send control signals to the neural stimulator circuitry 206 for transmitting electrical stimulation pulses to the electrodes 204. The controller circuitry 212 analyzes the determined physiological parameters and other parameters inputted by the user using the programmer 104 to assess appropriate therapy regime and send control signals to neural stimulation circuitry 206 for transmitting stimulation pulses to the patient's target tissue.

The transceiver/telemetry circuitry 214 may communicate the determined physiological parameters to the programmer 104 located external to the patient's body. The telemetry circuitry 214 may use a suitable communication protocol, such as, the medical implant communication service (MICS) in the bandwidth of 402-405 MHz, for communicating with the programmer 104.

The memory 216 may be used to store the stimulation parameters received from programmer 104 and the physiological parameters determined by the sensor circuitry 210. For example, the memory 216 can store at least one year of daily lead impedance measurements and/or program usage. In another example, the memory can store lifetime energy use data for the device. In yet another example, the memory may store a list of measurements over time of a sensed parameter, for example, heart rate, for assessing the appropriate therapy regime.

The IMD 102 can be encased in a biocompatible metallic, polymeric, or composite housing (not shown), according to various embodiments. The housing protects the components of the IMD 102 from coming in contact with the patient's tissue. Additionally, the IMD 102 includes a power source such as a battery for delivering power to the IMD 102.

Figure 3:
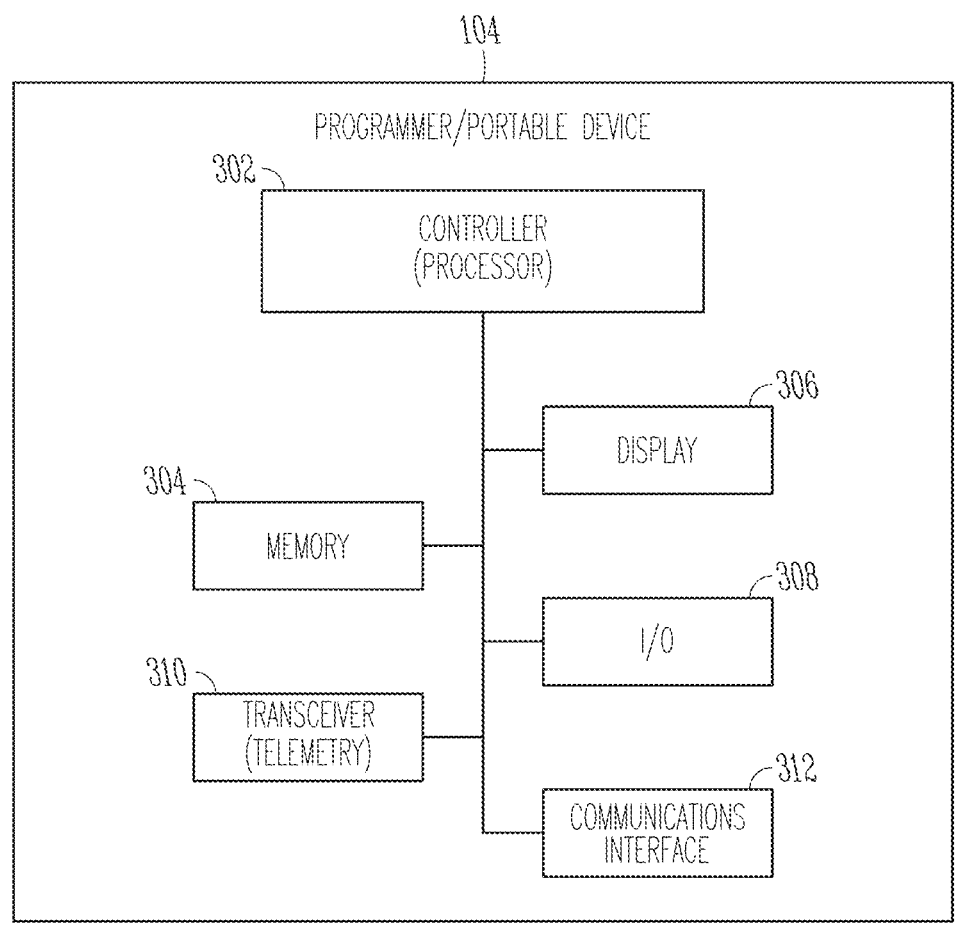
FIG. 3 illustrates an example of an external device, such as the programmer of FIG. 1.

FIG. 3 illustrates an example of an external device such as the programmer 104 of FIG. 1. The programmer 104 may be a portable device or hand held device that includes a controller/processor 302, a memory 304, a display 306, an input/output (I/O) unit 308, a transceiver/telemetry unit 310, and a communications interface 312. The programmer 104 may be housed within a polymeric, metallic or composite housing. The controller 302 may control various operations of the programmer 104. The controller 302 may include any suitable computing device, for example, microprocessors, microcomputers, microcontrollers, digital signal processors, central processing units, state machines, logic circuitries, and/or any devices that manipulate signals based on operational instructions. Among other capabilities, the controller 302 may be configured to fetch and execute computer-readable instructions stored in the memory 304. Further, the controller 302 may be configured with standard or customized operating systems, such as, Microsoft Windows, Linux, UNIX, or the like, with one or more custom software installed to control the operations of other components of the programmer 104. The controller 302 may be a fixed or portable computing device such as a desktop computer or a laptop, tablet or phone. The telemetry unit 310 communicates with the IMD 102 using the telemetry link 106 (FIG. 1). In some embodiments, the telemetry unit 310 allows the programmer 104 to control and program the IMD 102. In addition, the telemetry unit 310 allows the programmer 104 to communicate with the IMD 102 (shown in FIG. 2).

Figure 4:
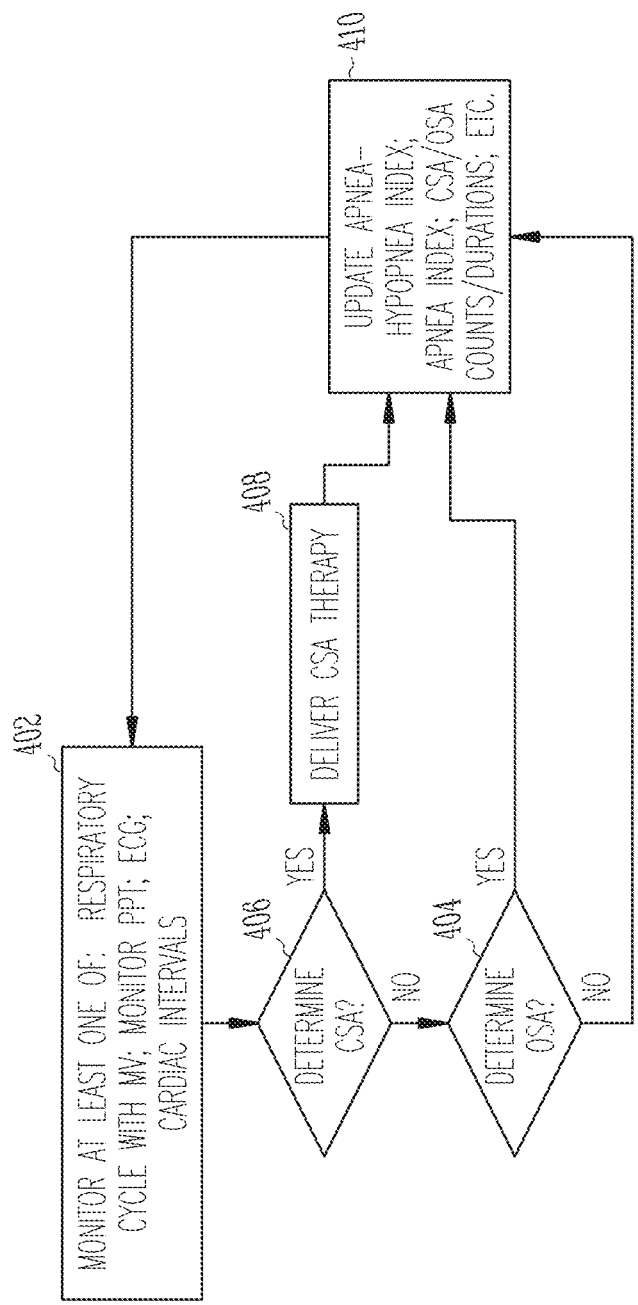
FIG. 4 illustrates a flow diagram for an example of a method of identifying apnea and delivering therapy for the identified CSA apnea, according to various embodiments of the present subject matter.
Figure 5A:
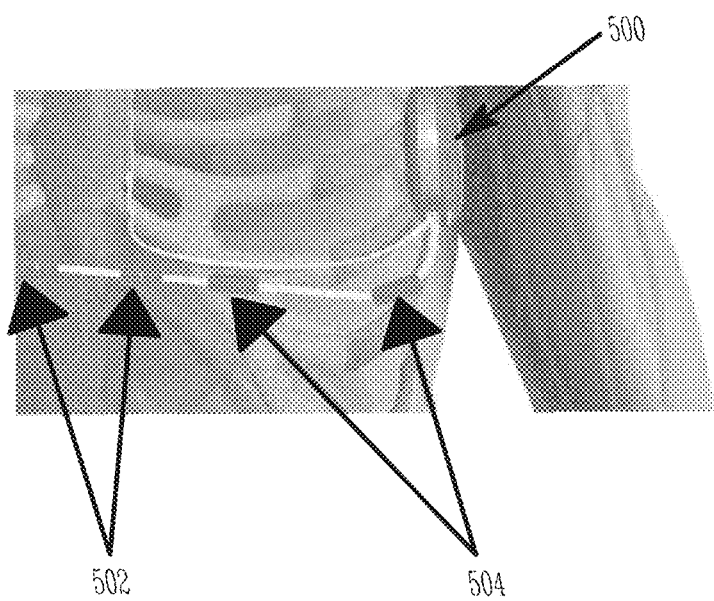
FIGS. 5A-5C illustrates an example of a subcutaneous implantable cardiac defibrillator (S-ICD) for delivering apnea therapy stimulation, according to various embodiments of the present subject matter.
Figure 5B:
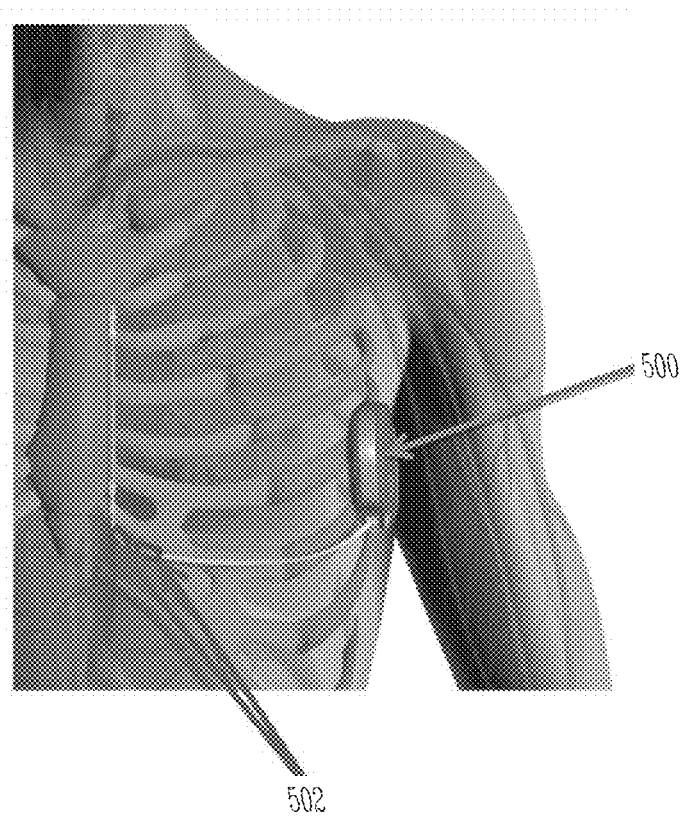
Figure 5C:
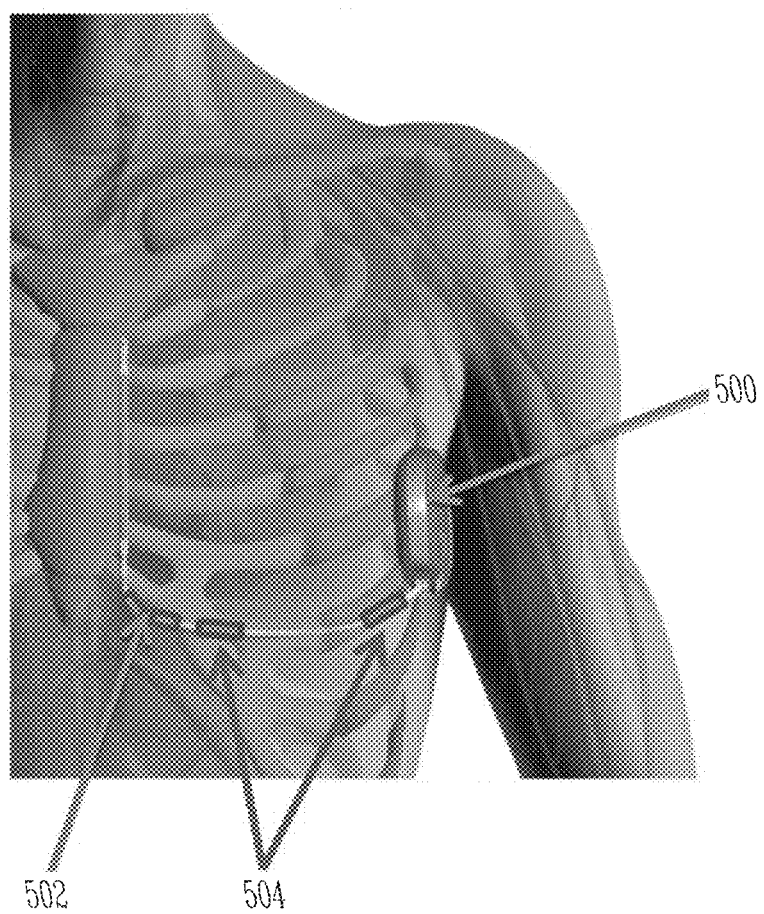

FIG. 4 illustrates a flow diagram for an example of a method of identifying apnea and delivering therapy for the identified CSA apnea, according to various embodiments of the present subject matter. At 402, real-time or near real-time discrimination includes monitoring at least one of: respiratory cycle with minute ventilation (MV), pulse transit time (PTT), electrocardiogram (ECG), S1/S3 heart sounds and cardiac intervals. If CSA is determined at 406, therapy is delivered for the CSA at 408 and an apnea-hypopnea index is updated at 410. In various embodiments, an apnea index includes CSA and OSA counts, durations, etc. If no CSA is determined at 406, then a determination is made of OSA at 404. If OSA is determined at 404, an apnea-hypopnea index is updated at 410. If no OSA is determined at 404, then an apnea-hypopnea index is updated at 410. Once apnea is determined and discriminated, the appropriate therapy can be applied in a closed loop system. Examples of CSA therapy may include stand-alone phrenic nerve stimulation, phrenic nerve stimulation combined with CRM or diaphragm stimulation in various embodiments. The stimulation may be delivered using an LV lead, a phrenic nerve lead, or a controlled pacing seed in various embodiments. Phrenic nerve stimulation may also be combined with diaphragm stimulation via electrodes on an S-ICD lead or seed, in various embodiments. Various embodiments include cough reflex stimulation via the vagus nerve for CSA therapy. Phrenic nerve stimulation for CSA therapy may include stimulation of the right brachiocephalic vein or stimulation of the left pericardiophrenic vein, in various embodiments. Phrenic nerve stimulation may also include an S-ICD electrode tunneled to sternum, as a motor point for the diaphragm is located next to the hole for the inferior vena cava (IVC). The S-ICD lead may be modified with additional electrodes and/or the implant location can be modified to enable stimulation of phrenic/motor points. Additional embodiments may include dedicated electrodes tunneled or placed on one or both hemidiaphragms (for uni- or bi-lateral stimulation), or electrodes stented onto the IVC from inside at the level of the diaphragm to capture motor points FIGS. 5A-5C illustrates an example of a subcutaneous implantable cardiac defibrillator (S-ICD) for delivering apnea therapy stimulation, according to various embodiments of the present subject matter. The S-ICD 500 may include stimulation electrodes 502 and strain gauges 504 along a lead to assist in therapy delivery and sensing. FIGS. 5B and 5C illustrate electrodes 502 and/or strain gauges 504 along the S-ICD 500 lead. FIG. 5A illustrates electrodes 502 and/or strain gauges 504 along an additional dedicated lead. The strain gauges 504 may monitor breathing by detecting a level of expansion, instead of using MV or to complement MV in various embodiments.

According to various embodiments, a subcutaneous implantable cardiac defibrillator (S-ICD) device is provided. The device may include an input configured to receive a signal indicative of a real-time or near real-time determination of type of an apnea event for a patient during the apnea event, and a processor adapted to be connected to the input. The processor may be configured to use the signal to select therapy appropriate for the determined apnea type to be applied to the patient during the apnea event to treat the apnea event, withhold therapy inappropriate for the determined apnea type, or both select therapy appropriate for the determined apnea type and withhold therapy inappropriate for the determined apnea type. In various embodiments, the signal includes a determination of whether the apnea event is primarily an obstructive sleep apnea (OSA) event or primarily a central sleep apnea (CSA) event. The S-ICD device further comprises an electrode on a lead connected to the S-ICD device, where the S-ICD device is configured to deliver the selected therapy using the electrode in various embodiments.

Figure 6:
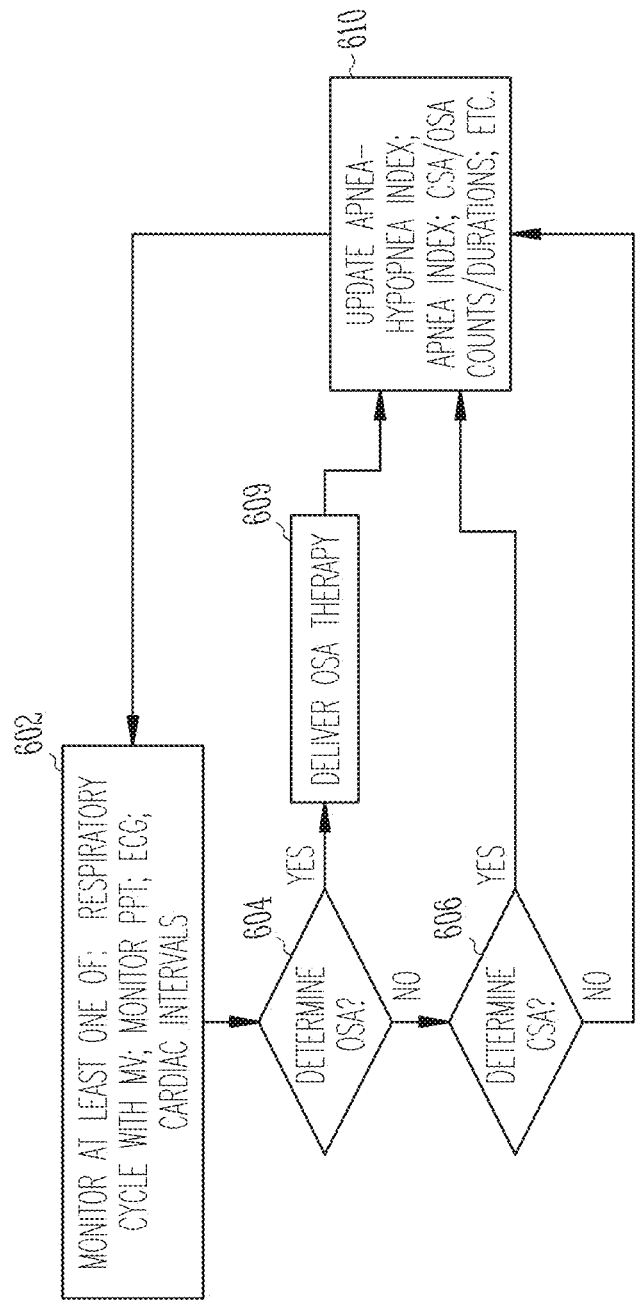
FIG. 6 illustrates a flow diagram for an example of a method of identifying apnea and delivering therapy for the identified OSA apnea, according to various embodiments of the present subject matter.

FIG. 6 illustrates a flow diagram for an example of a method of identifying apnea and delivering therapy for the identified OSA apnea, according to various embodiments of the present subject matter. At 602, real-time or near real-time discrimination includes monitoring at least one of: respiratory cycle with MV, PTT, ECG, S1/S3 heart sounds and cardiac intervals. If OSA is determined at 604, therapy is delivered for the OSA at 609 and an apnea-hypopnea index is updated at 610. In various embodiments, an apnea index includes CSA and OSA counts and/or durations for example. If no OSA is determined at 604, then a determination is made of CSA at 606. If CSA is determined at 606, an apnea-hypopnea index is updated at 610. If no CSA is determined at 606, then an apnea-hypopnea index is updated at 610. Once apnea is determined and discriminated, the appropriate therapy can be applied in a closed loop system. Examples of OSA therapy may include stand-alone hypoglossal nerve stimulation, alone or combined with CRM using a hypoglossal nerve lead, or combined with a controlled pacing seed, or combined with an S-ICD with pacing seed or lead at the hypoglossal nerve. A pacing seed can be used to provide stimulation via wireless communication with a master implantable device, where the implantable device controls the stimulation provided by the pacing seed. Another example of OSA therapy may include improving airway patency with laryngeal stimulation via VNS. Further examples of OSA therapy may include glossopharyngeal nerve, accessory nerve, and ansa cervicalis stimulation, in various embodiments.

Figure 7:
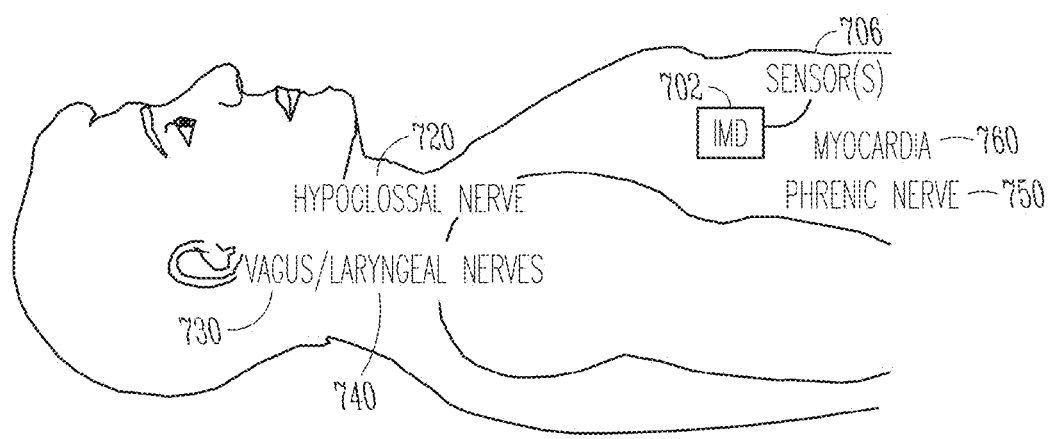
FIG. 7 illustrates an example of a device for delivering apnea therapy stimulation, according to various embodiments of the present subject matter.
Figure 10:
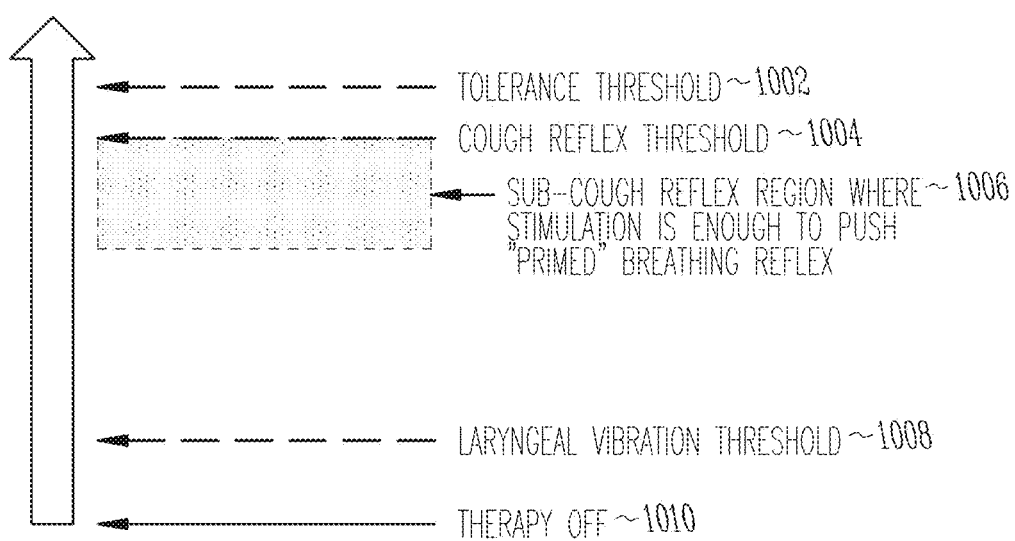
FIG. 10 illustrates an example of cough reflex vagal nerve stimulation for apnea therapy, according to various embodiments of the present subject matter.

FIG. 7 illustrates an example of a device for delivering apnea therapy stimulation, according to various embodiments of the present subject matter. Some embodiments may use a system of more than one IMD 702 to provide the desired therapies. The device may be an IMD 702 subcutaneously implanted within the patient. The IMD may include sensors 706 for detecting respiration or other parameters, which may be used to detect the apnea type. FIG. 7 also generally illustrates different potential stimulation targets. For example, an obstructive apnea therapy may stimulate hypoglossal nerve 720 or stimulate laryngeal muscles via stimulation of a laryngeal branch 740 of the vagus nerve 730 or of a vagus nerve at an intensity that causes laryngeal vibrations as shown in FIG. 10, and a central apnea therapy may stimulate a phrenic nerve 750 or myocardial 760 or may stimulate a vagus nerve 730 at an intensity, higher than the intensity that cause laryngeal vibration, to cause a cough or almost cause a cough. Hypoglossal stimulation may be used to keep an airway open. The hypoglossal is nearly entirely motor nerve fibers, so a patient feels little or no discomfort during stimulation. Stimulation of the larynx may also help keep the airway open by preventing the muscles in the region from relaxing, in various embodiments. Selective stimulation techniques may be used to stimulate hypoglossal and/or laryngeal nerves only on determining OSA, in various embodiments. Hypoglossal and laryngeal nerves may also be stimulated upon detection of respiratory cycle by MV or strain gauge, to prevent an obstruction block rather than waiting for one to occur, in an embodiments. In one embodiment, hypoglossal and laryngeal nerves may also be stimulated during a predicted time frame based on average of previous respiratory cycles. This predicted time frame mechanism may also be used for stimulating the diaphragm for a CSA event, in an embodiment.

Figure 8:
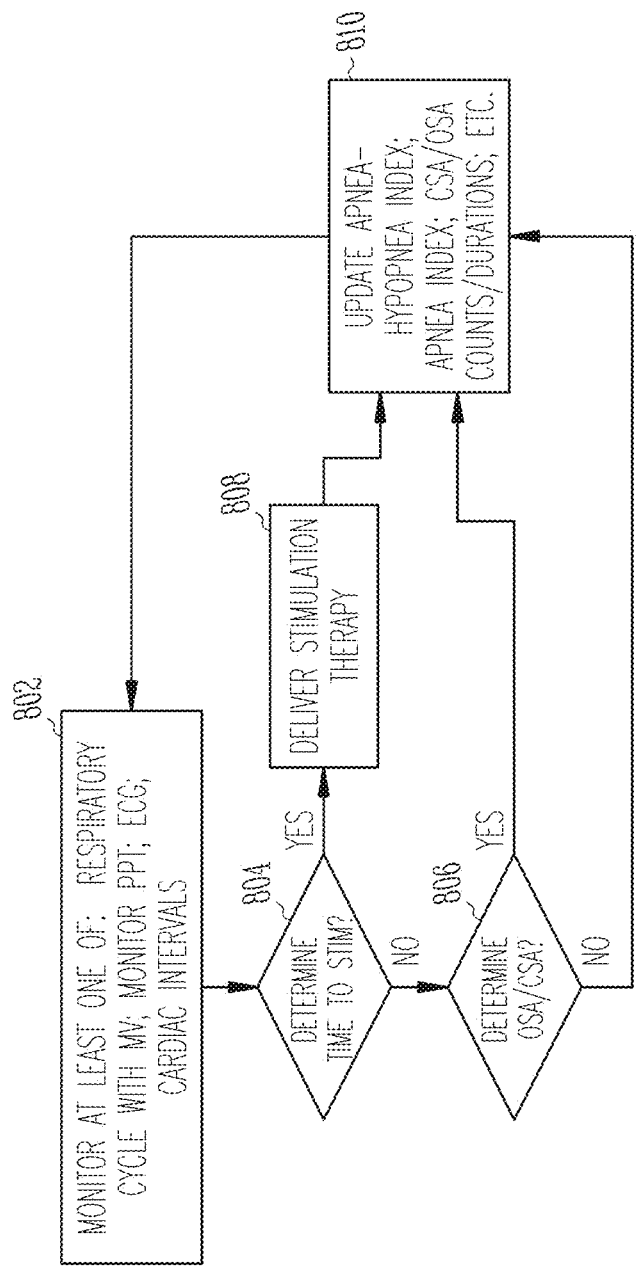
FIG. 8 illustrates a flow diagram for an example of a method of delivering apnea therapy stimulation, according to various embodiments of the present subject matter.

FIG. 8 illustrates a flow diagram for an example of a method of delivering apnea therapy stimulation, according to various embodiments of the present subject matter. At 802, real-time or near real-time discrimination includes monitoring at least one of: respiratory cycle with MV, PTT, ECG, S1/S3 heart sounds and cardiac intervals. If time to stimulate is determined at 604, therapy is delivered at 808 and an apnea-hypopnea index is updated at 810. In various embodiments, an apnea index includes CSA and OSA counts, durations, etc. If no time to stimulate is determined at 804, then a determination is made of OSA or CSA at 806. If OSA/CSA is determined at 806, an apnea-hypopnea index is updated at 810. If no OSA/CSA is determined at 806, then an apnea-hypopnea index is updated at 810. For OSA, hypoglossal and laryngeal nerves may be stimulated upon detection of respiratory cycle by MV or strain gauge, to prevent an obstruction block rather than waiting for one to occur, in an embodiments. In various embodiments, time of day, posture, activity, and/or sleep sensor information can be used to gate when therapy is delivered to prevent unwanted stimulation during awake states for a patient. In one embodiment, hypoglossal and laryngeal nerves may also be stimulated during a predicted time frame based on average of previous respiratory cycles. This predicted time frame mechanism may also be used for stimulating the diaphragm for a CSA event, in an embodiment.

Figure 9:
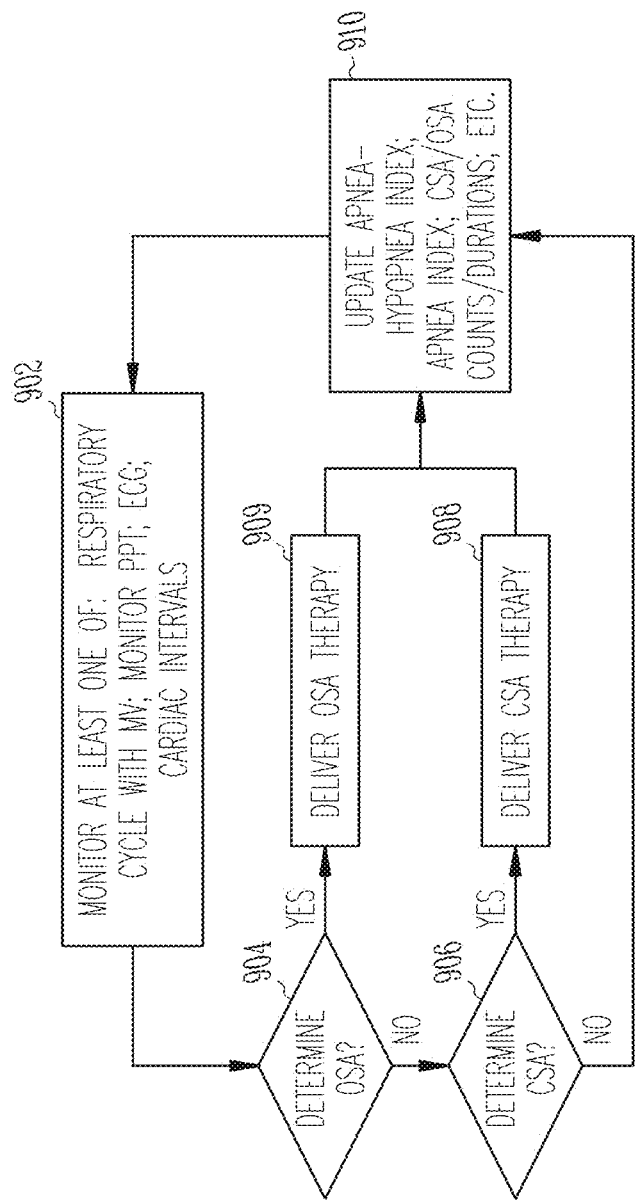
FIG. 9 illustrates a flow diagram for an example of a method of delivering apnea therapy stimulation for both CSA and OSA, according to various embodiments of the present subject matter.

FIG. 9 illustrates a flow diagram for an example of a method of delivering apnea therapy stimulation for both CSA and OSA, according to various embodiments of the present subject matter. At 902, real-time or near real-time discrimination includes monitoring at least one of: respiratory cycle with MV, PTT, ECG, S1/S3 heart sounds and cardiac intervals. If OSA is determined at 904, therapy is delivered for the OSA at 909 and an apnea-hypopnea index is updated at 910. In various embodiments, an apnea index includes CSA and OSA counts, durations, etc. If no OSA is determined at 904, then a determination is made of CSA at 906. If CSA is determined at 906, therapy is delivered for the CSA at 908 and an apnea-hypopnea index is updated at 910. If no CSA is determined at 906, then an apnea-hypopnea index is updated at 910. Sleep apnea patients fall on a spectrum of CSA/OSA, usually not exclusively one or the other. Various embodiments may include treatment using a determined type of apnea event, including: VNS to induce cough reflex for CSA, VNS to induce laryngeal vibration or other local nerve stimulation for OSA, VNS for CSA plus hypoglossal lead for OSA, pacing seeds including hypoglossal for OSA and phrenic for CSA controlled by a central IMD, or atrial overdrive pacing. VNS for OSA may include using selective fiber techniques and dropping avoidance mechanisms briefly to obtain laryngeal vibration or hypoglossal stimulation depending on electrode position.

FIG. 10 illustrates an example of cough reflex vagal nerve stimulation (VNS) for apnea therapy, according to various embodiments of the present subject matter. Various embodiments described herein may stimulate the vagus nerve to elicit laryngeal vibration for an obstructive apnea therapy, or may stimulate the vagus nerve to elicit a cough or at least elicit the inspiratory breath (primed breath) in preparation expiratory flow of the cough. At level 1010, the therapy is not delivered. Some of the first axons to be captured with the cervical vagus nerve is stimulated are those axons that innervate the laryngeal muscles. Thus, increasing the level of stimulation to 1008 reaches the laryngeal vibration threshold. At level 1004, as additional axons of the cervical vagus nerve are captured by increasing the intensity (e.g. current) of the vagal stimulation, the cough reflex threshold is reached. The patient is only able to tolerate a certain intensity of vagal stimulation, and this limit may vary from patient-to-patient. This limit is generally represented at level 1002 ("tolerance threshold"). Between level 1006 and 1004 lies the sub-cough reflex region that may be used for the present therapy, in which stimulation is sufficient to trigger a "primed" breathing reflex to treat apnea in various embodiments. The primed breathing reflex includes inspiratory breath in preparation for the expiratory flow of the cough. Selective fiber stimulation, where select axons of the cervical vagus nerve are stimulated and other axons are not stimulated, may allow cough reflex to occur at levels below the tolerance threshold, in an embodiment.

According to various embodiments, a method for apnea therapy for an apnea event is provided. The method may include stimulating a vagus nerve at a first intensity to treat an obstructive sleep apnea (OSA) event, wherein stimulating the vagus nerve at the first intensity induces laryngeal vibrations but not cough, or stimulating the vagus nerve at a second intensity to treat a central sleep apnea (CSA) event, wherein stimulating the vagus nerve at the second intensity induces a cough reflex or induces a primed breathing reflex in preparation for a cough. In various embodiments, stimulating the vagus nerve includes stimulating the cervical vagus nerve. In various embodiments, stimulating the vagus nerve includes stimulating selective fibers of the vagus nerve and not stimulating other fibers of the vagus nerve, wherein stimulating selective fibers of the vagus nerve induces laryngeal vibrations to treat the OSA event. Various embodiments may use different types or strengths of vagal nerve stimulation. If a type of the apnea event is primarily obstructive sleep apnea (OSA), the method may include stimulating a vagus nerve at a first intensity to cause laryngeal vibrations to treat the OSA in an embodiment. If the type of the apnea event is primarily central sleep apnea (CSA), the method may include stimulating the vagus nerve at a second intensity to cause a cough reflex to treat the CSA in an embodiment.

Figure 11:
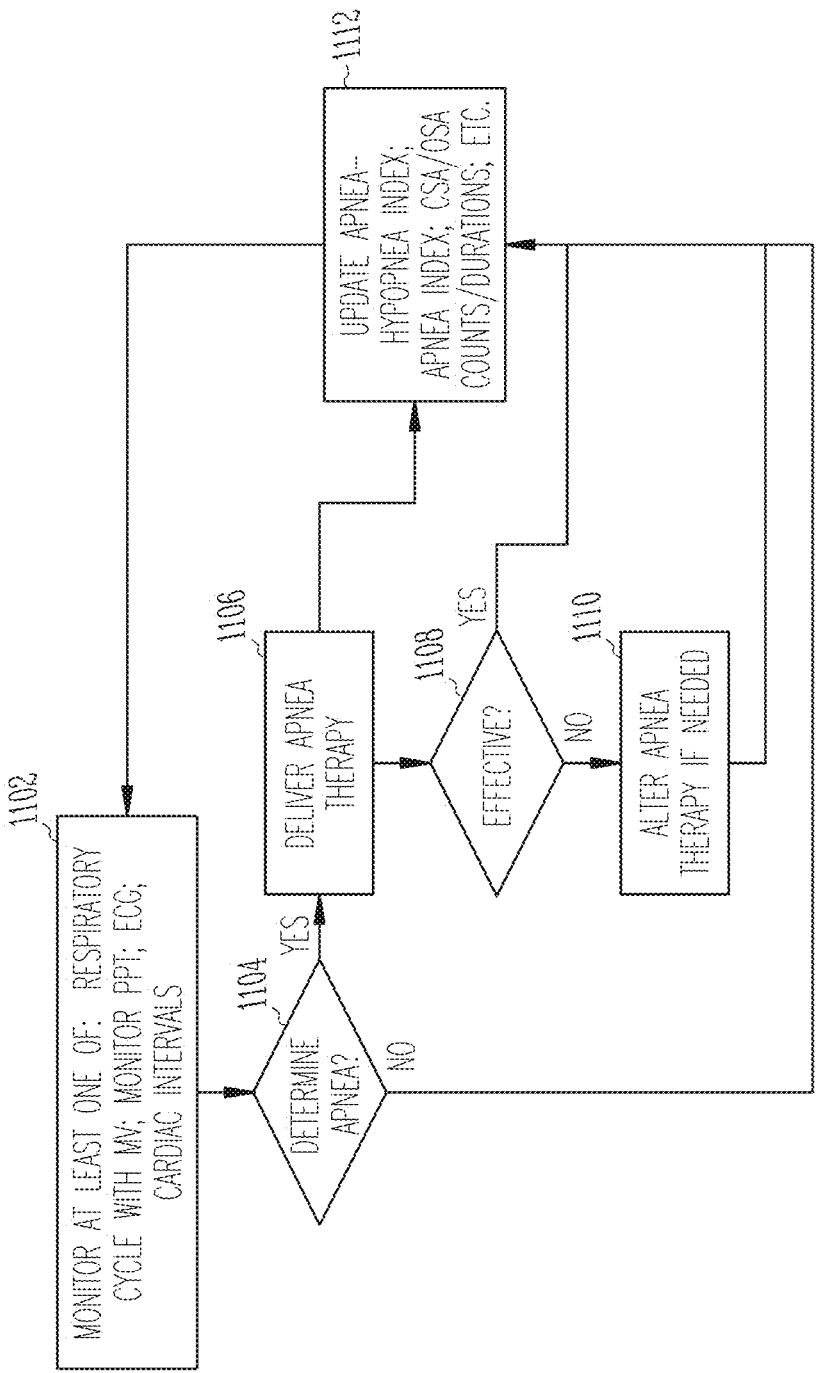
FIG. 11 illustrates a flow diagram for an example of a method of delivering apnea therapy stimulation and determining effectiveness of the delivered therapy, according to various embodiments of the present subject matter.

FIG. 11 illustrates a flow diagram for an example of a method of delivering apnea therapy stimulation and determining effectiveness of the delivered therapy, according to various embodiments of the present subject matter. At 1102, real-time or near real-time discrimination includes monitoring at least one of: respiratory cycle with MV, PTT, ECG, S1/S3 heart sounds and cardiac intervals. If apnea (CSA or OSA) is determined at 1104, therapy is delivered for the apnea at 1106 and an apnea-hypopnea index is updated at 1112. At 1108, a determination is made of whether the therapy is effective. If the therapy is effective, an apnea-hypopnea index is updated at 1112. If the therapy is not effective, the therapy is altered at 1110 and an apnea-hypopnea index is updated at 1112. Altering the therapy may include changing an intensity or other stimulation parameter of the therapy, or may include changing to a different type of apnea therapy (such as change from stimulating hypoglossal nerve to stimulating vagus nerve by way of example and not limitation). In various embodiments, an apnea index includes CSA and OSA counts, durations, etc. If no apnea is determined at 1104, then an apnea-hypopnea index is updated at 1112. Respiratory sensing feedback (such as MV) may be used to verify whether stimulation therapy (for OSA only, CSA only, or both OSA/CSA therapies) has been effective in treating apnea, in various embodiments. Subsequent modification of one or more therapies may be initiated if effectiveness is below a programmable threshold, in an embodiment.

Once apnea type is determined or discriminated, the appropriate therapy can be applied in a closed loop system. Examples of such apnea determination using airway patency may be found in co-pending, commonly assigned, U.S. Patent Application Ser. No. 61/975,084, entitled "DISCRIMINATION OF APNEA TYPE BY MEDICAL DEVICE", filed on Apr. 4, 2014, which is hereby incorporated by reference in its entirety. This subject matter refers to a method for real-time or near real-time apnea discrimination. These terms indicate that, although there may be some processing delays, the apnea discrimination is able to process the apnea events as they occur without an observable delay (e.g. real time) or with observable delays that are insignificant for processing the apnea events as they occur (near real time). Additional implanted sensors may be used to further augment CSA/OSA classification, such as spectral analysis of S1/S3 heart sounds (amplitudes), pulse transit time (ECG/cervical impedance plethysmography), ECG-based spectral analysis, and cardiac interbeat interval time series, in various embodiments.

The present subject matter may provide clinician guidance on determining that patient's therapy (CPAP type/settings; phrenic or hypoglossal stimulation; etc.). This stimulation therapy may be in any medical device (brady, tachy, VNS, S-ICD, monitor, etc.), including external medical devices and/or implantable medical devices in various embodiments.

VARIOUS EXAMPLES

An example (e.g. "Example 1") of an implantable medical device for apnea directed therapy may include an input configured to receive a signal indicative of a real-time or near real-time determination of type of an apnea event for a patient during the apnea event, and a processor adapted to be connected to the input. The processor may be configured to use the signal to select therapy appropriate for the determined apnea type to be applied to the patient during the apnea event to treat the apnea event, withhold therapy inappropriate for the determined apnea type, or both select therapy appropriate for the determined apnea type and withhold therapy inappropriate for the determined apnea type.

In Example 2, the subject matter of Example 1 may optionally be configured such that the signal includes a determination of whether the apnea event is primarily an obstructive sleep apnea (OSA) event or primarily a central sleep apnea (CSA) event.

In Example 3, the subject matter of Example 2 may optionally be configured such that, if the apnea event is determined to be primarily an OSA event, the selected therapy includes at least one of hypoglossal nerve stimulation or vagal nerve stimulation (VNS).

In Example 4, the subject matter of Example 2 may optionally be configured such that, if the apnea event is determined to be primarily an OSA event, the withheld therapy includes at least one of phrenic nerve stimulation, stimulation using a cardiac rhythm management (CRM) device, VNS cough reflex stimulation, or diaphragmatic stimulation.

In Example 5, the subject matter of Example 3 may optionally be configured such that the VNS includes laryngeal stimulation.

In Example 6, the subject matter of any one or any combination of Example 3 or Example 5 may optionally be configured such that the VNS includes selective fiber stimulation.

In Example 7, the subject matter of Example 1 may optionally be configured such that the processor is configured to control a stimulator to apply electrical stimulation therapy in a closed loop system.

In Example 8, the subject matter of Example 2 may optionally be configured such that, if the apnea event is determined to be primarily a CSA event, the selected therapy includes at least one of phrenic nerve stimulation, stimulation using a CRM device, VNS cough reflex stimulation, or diaphragmatic stimulation.

In Example 9, the subject matter of Example 2 may optionally be configured such that, if the apnea event is determined to be primarily a CSA event, the withheld therapy includes at least one of hypoglossal nerve stimulation or vagal nerve stimulation (VNS).

In Example 10, the subject matter of Example 2 may optionally be configured such that, if the apnea event is determined to be primarily a CSA event, the electrical stimulation therapy includes phrenic nerve stimulation in combination with using a CRM device.

In Example 11, the subject matter of Example 2 may optionally be configured such that, if the apnea event is determined to be primarily a CSA event, the electrical stimulation therapy includes VNS reflex cough stimulation.

In Example 12, the subject matter of any one or any combination of Examples 1-11 may optionally be configured such that the processor is configured to select a stimulation site based on the received signal.

In Example 13, the subject matter of any one or any combination of Examples 1-12 may optionally be configured such that the implantable medical device includes a neurostimulator.

In Example 14, the subject matter of any one or any combination of Examples 1-13 may optionally be configured such that the device further includes a remote stimulator controlled by the implantable medical device.

In Example 15, the subject matter of any one or any combination of Examples 1-14 may optionally be configured such that the implantable medical device includes a subcutaneous implantable cardiac defibrillator (S-ICD).

An example (e.g. "Example 16") of a method for apnea directed therapy may include receiving a signal indicative of a real-time or near real-time determination of type of an apnea event for a patient during the apnea event, using the signal to select appropriate electrical stimulation therapy to be applied to the patient during the apnea event to treat the apnea event, and applying the electrical stimulation therapy in a closed loop system.

In Example 17, the subject matter of Example 16 may optionally be configured such that the signal includes a determination of whether the apnea event is primarily an obstructive sleep apnea (OSA) event or primarily a central sleep apnea (CSA) event.

In Example 18, the subject matter of Example 17 may optionally be configured such that, if the apnea event is determined to be primarily an OSA event, applying electrical stimulation therapy includes applying hypoglossal nerve stimulation.

In Example 19, the subject matter of Example 17 may optionally be configured such that, if the apnea event is determined to be primarily an OSA event, applying electrical stimulation therapy includes applying vagal nerve stimulation (VNS).

In Example 20, the subject matter of Example 19 may optionally be configured such that applying VNS includes applying laryngeal stimulation.

In Example 21, the subject matter of Example 19 may optionally be configured such that applying VNS includes using selective fiber stimulation.

In Example 22, the subject matter of Example 17 may optionally be configured such that, if the apnea event is determined to be primarily an OSA event, applying electrical stimulation therapy includes applying hypoglossal nerve stimulation in combination with applying VNS.

In Example 23, the subject matter of Example 17 may optionally be configured such that, if the apnea event is determined to be primarily a CSA event, applying electrical stimulation therapy includes applying phrenic nerve stimulation.

In Example 24, the subject matter of Example 17 may optionally be configured such that, if the apnea event is determined to be primarily a CSA event, applying electrical stimulation therapy includes using a cardiac rhythm management (CRM) device In Example 25, the subject matter of Example 17 may optionally be configured such that, if the apnea event is determined to be primarily a CSA event, applying electrical stimulation therapy includes applying phrenic nerve stimulation in combination with using a CRM device.

In Example 26, the subject matter of Example 17 may optionally be configured such that, if the apnea event is determined to be primarily a CSA event, applying electrical stimulation therapy includes applying VNS reflex cough stimulation.

In Example 27, the subject matter of Example 16 may optionally be configured such that the method further includes selecting a stimulation site based on the received signal.

In Example 28, the subject matter of Example 16 may optionally be configured such that applying electrical stimulation includes using an implantable medical device (IMD).

An example (e.g. "Example 29") of an implantable medical device for apnea directed therapy may include an input configured to receive a signal indicative of a real-time or near real-time determination of type of an apnea event for a patient during the apnea event, and a processor adapted to be connected to the input. The processor may be configured to use the signal to perform at least one of: selecting therapy appropriate for the determined apnea type to be applied to the patient during the apnea event to treat the apnea event; or withholding therapy inappropriate for the determined apnea type.

In Example 30, the subject matter of Example 29 may optionally be configured such that the signal includes a determination of whether the apnea event is primarily an obstructive sleep apnea (OSA) event or primarily a central sleep apnea (CSA) event.

In Example 31, the subject matter of Example 30 may optionally be configured such that, if the apnea event is determined to be primarily an OSA event, the selected therapy includes at least one of hypoglossal nerve stimulation or vagal nerve stimulation (VNS).

In Example 32, the subject matter of Example 30 may optionally be configured such that, if the apnea event is determined to be primarily an OSA event, the withheld therapy includes at least one of phrenic nerve stimulation, stimulation using a cardiac rhythm management (CRM) device, VNS cough reflex stimulation, or diaphragmatic stimulation.

In Example 33, the subject matter of Example 29 may optionally be configured such that the processor is configured to control a stimulator to apply electrical stimulation therapy in a closed loop system.

In Example 34, the subject matter of Example 30 may optionally be configured such that, if the apnea event is determined to be primarily a CSA event, the selected therapy includes at least one of phrenic nerve stimulation, stimulation using a CRM device, VNS cough reflex stimulation, or diaphragmatic stimulation.

In Example 35, the subject matter of Example 30 may optionally be configured such that, if the apnea event is determined to be primarily a CSA event, the withheld therapy includes at least one of hypoglossal nerve stimulation or vagal nerve stimulation (VNS).

An example (e.g. "Example 36") of a method for apnea therapy for an apnea event may include stimulating a vagus nerve at a first intensity to treat an obstructive sleep apnea (OSA) event, wherein stimulating the vagus nerve at the first intensity induces laryngeal vibrations but not cough or stimulating the vagus nerve at a second intensity to treat a central sleep apnea (CSA) event, wherein stimulating the vagus nerve at the second intensity induces a cough reflex or induces a primed breathing reflex in preparation for a cough.

In Example 37, the subject matter of Example 36 may optionally be configured such that stimulating the vagus nerve includes stimulating the cervical vagus nerve.

In Example 38, the subject matter of Example 36 may optionally be configured such that stimulating the vagus nerve includes stimulating selective fibers of the vagus nerve and not stimulating other fibers of the vagus nerve, wherein stimulating selective fibers of the vagus nerve induces laryngeal vibrations to treat the OSA event.

An example (e.g. "Example 39") of a subcutaneous implantable cardiac defibrillator (S-ICD) device may include an input configured to receive a signal indicative of a real-time or near real-time determination of type of an apnea event for a patient during the apnea event, and a processor adapted to be connected to the input. The processor may be configured to use the signal to select therapy appropriate for the determined apnea type to be applied to the patient during the apnea event to treat the apnea event, withhold therapy inappropriate for the determined apnea type, or both select therapy appropriate for the determined apnea type and withhold therapy inappropriate for the determined apnea type. The signal may be configured to include a determination of whether the apnea event is primarily an obstructive sleep apnea (OSA) event or primarily a central sleep apnea (CSA) event.

In Example 40, the subject matter of Example 39 may optionally be configured such that the device further includes an electrode on a lead connected to the S-ICD device, wherein the S-ICD device is configured to deliver the selected therapy using the electrode.

One of ordinary skill in the art will understand that the modules and other circuitry shown and described herein can be implemented using software, hardware, and/or firmware. Various disclosed methods may be implemented as a set of instructions contained on a computer-accessible medium capable of directing a processor to perform the respective method.

This application is intended to cover adaptations or variations of the present subject matter. It is to be understood that the above description is intended to be illustrative, and not restrictive. For example, the present subject matter can be applied to other medical procedures where heating or ablation of tissue is desired. The scope of the present subject matter should be determined with reference to the appended claims, along with the full scope of legal equivalents to which such claims are entitled.

What is claimed is:

1. A method for apnea directed therapy, the method comprising:
   receiving a signal indicative of a real-time or near real-time apnea event for a patient;
   processing the signal to classify the apnea event as a mixed central sleep apnea (CSA)/obstructive sleep apnea (OSA) event;
   using the classified apnea event to select appropriate electrical stimulation therapy to be applied to the patient during the apnea event to treat the classified apnea event; and
   applying the electrical stimulation therapy in a closed loop system.

2. The method of claim 1, further comprising processing the signal to classify another apnea event as a primarily OSA event, wherein applying electrical stimulation therapy includes applying hypoglossal nerve stimulation when the classified apnea event is the primarily OSA event.

3. The method of claim 1, further comprising processing the signal to classify another apnea event as a primarily OSA event, wherein applying electrical stimulation therapy includes applying vagal nerve stimulation (VNS) when the classified apnea event is the primarily OSA event.

4. The method of claim 3, wherein applying VNS includes applying laryngeal stimulation.

5. The method of claim 3, wherein applying VNS includes applying laryngeal stimulation using selective fiber stimulation.

6. The method of claim 1, further comprising processing the signal to classify another apnea event as a primarily OSA event, wherein applying electrical stimulation therapy includes applying hypoglossal nerve stimulation in combination with applying VNS when the classified apnea event is the primarily OSA event.

7. The method of claim 1, further comprising processing the signal to classify another apnea event as a primarily CSA event, wherein applying electrical stimulation therapy includes applying phrenic nerve stimulation when the classified apnea event is the primarily CSA event.

8. The method of claim 1, further comprising processing the signal to classify another apnea event as a primarily CSA event, wherein applying electrical stimulation therapy includes using a cardiac rhythm management (CRM) device when the classified apnea event is the primarily CSA event.

9. The method of claim 1, further comprising processing the signal to classify another apnea event as a primarily CSA event, wherein applying electrical stimulation therapy includes applying phrenic nerve stimulation in combination with using a CRM device when the classified apnea event is the primarily CSA event.

10. The method of claim 1, further comprising processing the signal to classify another apnea event as a primarily CSA event, wherein applying electrical stimulation therapy includes applying VNS reflex cough stimulation when the classified apnea event is the primarily CSA event.

11. The method of claim 1, wherein applying electrical stimulation therapy includes applying stimulation to treat CSA and applying stimulation to treat OSA when the classified apnea event is the mixed CSA/OSA event.

12. The method of claim 11, wherein applying stimulation to treat CSA and applying stimulation to treat OSA after applying stimulation to treat CSA when the classified apnea event is the mixed CSA/OSA event.

13. The method of claim 11, wherein applying stimulation to treat CSA includes stimulating a diaphragm.

14. The method of claim 13, wherein applying stimulation to treat OSA includes stimulating to correct mechanical timing between the diaphragm and throat.

\* \* \* \* \*